Figure 1:
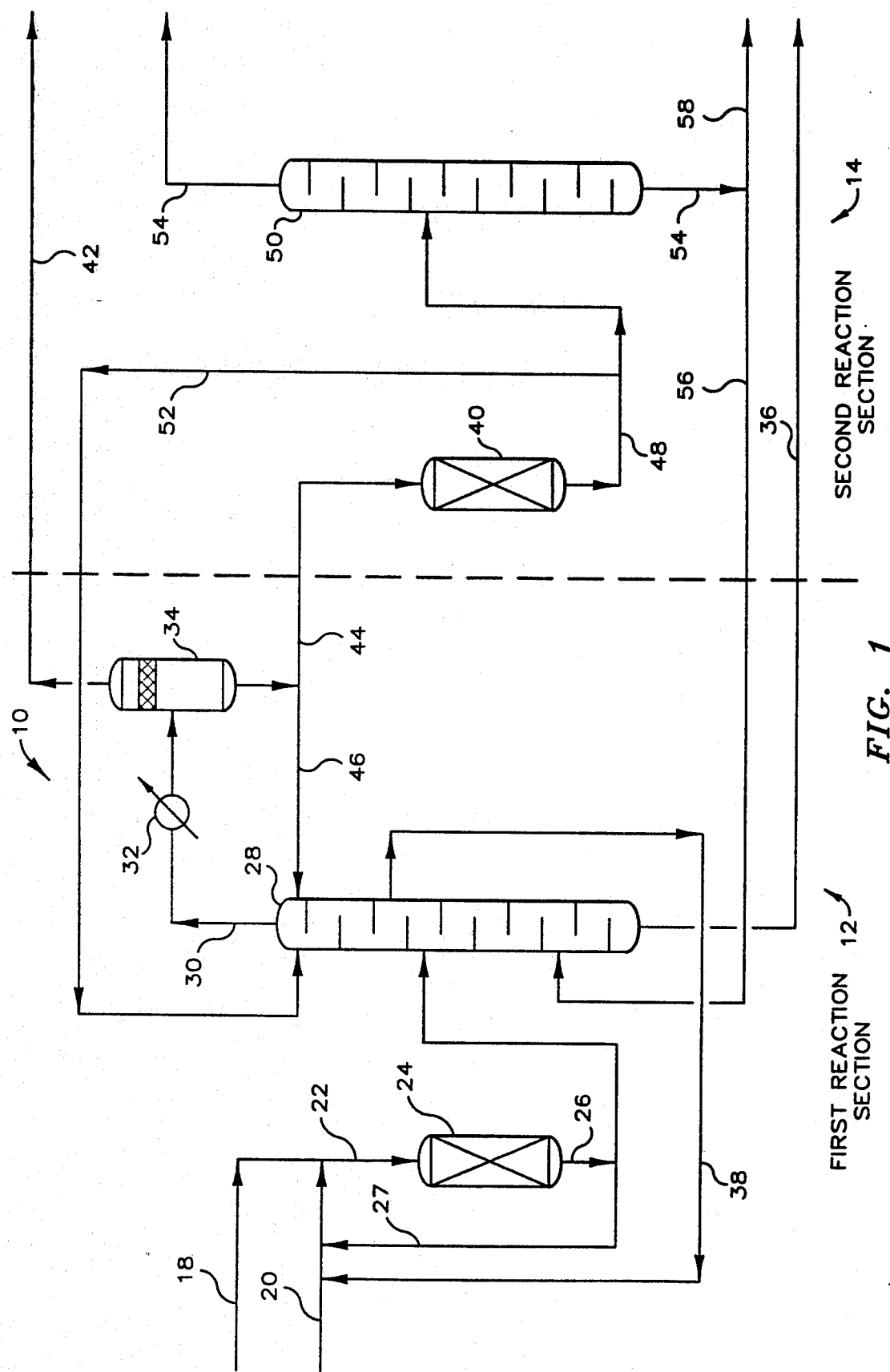

United States Patent [19]

Zahn

[11] Patent Number: 5,245,087

[45] Date of Patent: Sep. 14, 1993

[54] ETHERIFICATION PROCESS

[75] Inventor: Carl W. Zahn, Bartlesville, Okla.

[73] Assignee: Phillips Petroleum Company, Bartlesville, Okla.

[21] Appl. No.: 953,385

[22] Filed: Sep. 30, 1992

[51] Int. Cl.$^5$ .............................................. C07C 41/06
[52] U.S. Cl. .................................................. 568/697
[58] Field of Search ........................................ 568/697

[56] References Cited

U.S. PATENT DOCUMENTS

| | | | |
|---|---|---|---|
| 3,119,766 | 1/1964 | Voltz et al. | 208/291 |
| 3,979,461 | 9/1976 | Ancillotti et al. | 260/614 A |
| 4,193,770 | 3/1980 | Chase et al. | 44/56 |
| 4,299,999 | 11/1981 | Mikitenko et al. | 568/697 |
| 4,302,298 | 11/1981 | Mikitenko et al. | 203/75 |
| 4,503,265 | 3/1985 | Schleppinghoff et al. | 568/697 |
| 4,647,703 | 3/1987 | Torck et al. | 568/697 |
| 4,988,366 | 1/1991 | Harandi et al. | 44/449 |

*Primary Examiner*—Howard T. Mars
*Attorney, Agent, or Firm*—Charles W. Stewart

[57] ABSTRACT

An etherification process for reacting tertiary olefin compounds with primary alcohols to produce an ether product is described. The etherification process includes two reactor stages for producing ether compounds and providing high conversion across the etherification process of the tertiary olefin compounds at reduced energy consumption.

9 Claims, 1 Drawing Sheet

ETHERIFICATION PROCESS

This invention relates to the production of alkyl tertiary alkyl ether compounds.

It is known that alkyl tertiary alkyl ether compounds can be prepared by reacting primary or secondary alcohols with olefin compounds having a double bond on a tertiary carbon atom in the presence of an acidic ion exchange resin catalyst. The particularly more common etherification reactions are those that involve reacting methanol with either isobutylene or isoamylenes to form respectively methyl tertiary butyl ether (MTBE) and methyl tertiary amyl ether (TAME). These tertiary alkyl ether compounds are particularly useful as octane improvers for liquid fuels, especially gasoline. Also, because of the low vapor pressure of these compounds, they are particularly useful for reducing the vapor pressure of gasoline. Recent federal government regulations have resulted in the requirement that motor gasoline be reformulated to include greater concentration levels of oxygenate compounds of which tertiary alkyl ether compounds have been found to be especially suitable for assisting in compliance with these new federal regulations.

While processes for the production of high octane tertiary alkyl ethers have been known in the art, there still remains various problems with the known processes that have heretofore not been resolved by those skilled in the art. In particular, because standard etherification reactions are equilibrium type reactions, most etherification processes do not provide economical means for obtaining high olefin reaction conversions without incurring high energy and capital costs to obtain such high olefin conversions. Also, as is generally the case for most process technologies, it is desirable to have an etherification process that provides for high purity product streams produced at a low operating cost.

It is therefore an object of this invention to provide an etherification process that produces tertiary alkyl ethers at high olefin conversion rates but with low operating and capital costs.

It is another object of this invention to provide a high purity ether product at low operating cost of production.

The inventive process includes contacting methanol and a feedstream of tertiary olefins with an acid catalyst in a first etherification reaction zone so as to form a first reaction mixture containing ether, tertiary olefins, and alcohol. The first reaction mixture is passed to first separation means for separating the first reaction mixture into a first overhead stream containing alcohol, a first bottoms stream containing ether, and an intermediate stream containing tertiary olefins. The first overhead stream is contacted with an acid catalyst contained in a second etherification reaction zone so as to form a second reaction mixture containing ether while the intermediate stream is introduced into the feedstream to the first etherification reaction zone. The second reaction mixture is separated into a second overhead stream containing alcohol and a second bottoms stream containing ether.

Other objects, aspects and features of the present invention will be evident from the following detailed description of the invention, the claims and the drawings in which:

FIG. 1 is a schematic flow diagram illustrating the process of the invention.

The inventive process includes the use of at least two separate etherification reaction zones and at least two separation zones. Each of the reaction zones is defined by a reactor vessel containing therein a suitable etherification catalyst for promoting or catalyzing an etherification reaction between reactive tertiary olefin compounds and primary or secondary alcohols. A feedstream containing tertiary olefins and alcohols, preferably primary alcohols, is charged or fed to a first etherification reaction zone of the process wherein the feedstream is contacted with the etherification catalyst under suitable reaction conditions for promoting the reaction of the tertiary olefins and alcohols contained in the feedstream to produce a first etherification reactor effluent or mixture containing ethers, alcohols and tertiary olefins.

A portion of the first etherification reactor mixture can optionally be recycled to the feedstream to the first etherification reaction zone as a means for controlling the reaction temperature within the first reaction zone. The remaining portion of the first etherification reactor mixture, which can include the entire first etherification reactor effluent stream, is passed to first separation means defining a first separation zone and providing means for separating the first etherification reaction mixture into a first overhead stream, a first bottoms stream and an intermediate or sidedraw stream. The first bottoms stream comprises at least a portion of the ether compounds contained in the first etherification reactor mixture, and the first overhead stream comprises at least a portion of the alcohol compounds contained in the first etherification reactor mixture. As for the intermediate stream, it can comprise a portion of the tertiary olefin compounds contained in the first etherification reactor mixture.

In addition to the first overhead stream comprising at least a portion of the alcohol compounds contained in the first etherification reactor mixture, it can also contain a portion of the tertiary olefin compounds in the first etherification reactor mixture. The first overhead stream passes to a second etherification reaction zone wherein it is contacted with a suitable etherification catalyst for promoting or catalyzing an etherification reaction between the reactive tertiary olefin and alcohols contained in the first overhead stream and to form a second etherification reaction mixture. The second etherification reaction zone is defined by a second reactor vessel wherein contained is the etherification catalyst. The process conditions within the second etherification reaction zone are suitable for promoting the reaction of the tertiary olefins and alcohols contained in the first overhead stream when contacted with the etherification catalyst.

The first bottoms stream is an ether product stream containing at least a portion, preferably a major portion, of the ether reaction product produced in the first reaction step of the process. As for the intermediate stream, as earlier noted, it can comprise a portion of the tertiary olefin compounds contained in the first etherification reactor mixture, and it is preferred for the concentration of ether compounds in the intermediate stream to be minimized because of the positive benefits that result when the intermediate stream is recycled to the first reaction zone. As described elsewhere herein, because the etherification reaction is an equilibrium type reaction, the etherification reaction toward the production of ether compounds is favored when the concentration of ether in the reaction zone is minimized. Thus, using the sidedraw stream, having a lower concentration of ethers than that of the first reaction zone recycle stream, to control the reactor temperature also provides a benefit by improving the first reactor zone tertiary olefin conversion. It has also been found that the recycling of the sidedraw stream to the first reactor zone provides for a high olefin conversion etherification process having a substantially reduced energy requirement. Therefore, a crucial aspect of the inventive process is for an intermediate stream from first separation means to be recycled as a portion of the feedstream to the first reactor zone.

At least a portion of the second etherification reaction effluent, or mixture, passes to second separation means for separating the second etherification reactor mixture into a second overhead stream and a second bottoms stream. The second overhead stream comprises alcohols and generally includes components contained in the feedstream to the first reactor zone that are nonreactive and those tertiary olefin and alcohol components that pass through the reactor stages but remain unreacted. The remaining portion of the second etherification reaction mixture not fed to second separation means can, optionally, be passed as a fed, or as a reflux, to first separation means. One of the benefits from utilizing the sidedraw stream from first separation means as a recycle feed to the first reactor zone is that the quantity of overhead reflux for performing a desired separation in the case where first separation means is a fractional distillation unit is significantly, and unexpectedly, reduced to thereby lower the energy requirements for operating the unit. Additionally, the amount of the remaining portion of the second etherification reaction mixture fed to first separation means is reduced to thereby provide certain other operating benefits.

The second bottoms stream is an ether product stream, comprising ethers and, generally, at least a portion of the ethers contained in the at least a portion of the second etherification reaction mixture charged or fed to second separation means. As an additional embodiment of the inventive process, at least a portion of the second bottoms stream can optionally be passed to first separation means as a feed. It has been discovered that by charging the second bottoms stream to first separation means there is an improvement in the overall energy consumption in the two stage etherification process, presumably due to an improvement in separation efficiency of the separation means.

The feed to the first reaction section of the etherification process, as earlier described, is a mixed stream comprising a stream of primary or secondary alcohols and a stream having isoolefins and other compounds that are nonreactive in the presence of an acidic ion exchange resin catalyst at certain etherification reaction conditions. Generally, the isoolefins include those hydrocarbons having 4 to 16 carbon atoms per molecule. Examples of such isoolefins include isobutylene, isoamylene, isohexylene, isoheptylene, isooctylene, isononylene, isodecylene, isoundecylene, isododecylene, isotridecylene, isotetradecylene, isopentadecylene, and isohexadecylene, or mixtures of two or more thereof.

The alcohols which may be charged or fed to the first etherification reaction zone include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols, and glycerol, etc., or mixtures of two or more thereof.

The presently preferred reactants of the etherification process are methanol and isobutylene and/or an amylene because they respectively yield methyl tertiary butyl ether (MTBE) and methyl tertiary amyl ether (TAME). Accordingly, it is currently preferred for the isoolefins to be either predominantly isobutylene or predominantly isoamylene compounds with the double bond on the tertiary carbon atom of said isoamylene compounds, or both isobutylene and isoamylene, and the alcohol predominantly methanol.

It is generally preferred for the isoolefin and the alcohol to be passed through the etherification reaction zones in the presence of diluents which do not have an adverse effect upon the etherification reaction and which are nonreactive under the conditions of etherification. Examples of suitable diluents include alkanes and straight chain olefins. The feed to the reactors, excluding alcohol, is generally diluted so as to include from about 2 to about 80 weight percent isoolefin, preferably from about 10 to about 60 weight percent.

Any suitable molar ratio of alcohol to isoolefin in the feedstream to the etherification reactor zones can be utilized in this invention that will give the desired high tertiary olefin conversion sought to be achieved by the process of this invention. Generally, the molar ratio of alcohol to isoolefin in the feeds to the etherification reaction zones will be in the range of from about 0.5:1 to about 4:1; but, preferably, the molar ratio can range from about 0.8:1 to about 1.2:1. However, to achieve the highest conversion of the isoolefins in the process feeds to the etherification reaction zones, it is most preferable to have a molar ratio of alcohol to the isoolefin as close to 1:1 as is practically achievable.

Typical etherification reactions are well known in the art and are not a critical aspect of this invention except in the case of the second reaction zone where the operating pressure has an impact on the energy utilization of first separation means. The temperature for the etherification reaction zones and the space velocity for the feeds to the etherification reaction zones can be selected as desired depending upon the degree of olefin conversion sought; but, generally, they should be such to provide the highest degree of olefin conversion that is economically feasible. Generally, the temperature of the reaction zones will range upwardly to about 150° C. Preferably, the etherification reaction temperatures can range from about 30° C. to about 120° C., and most preferably, the temperature shall range from about 35° C. to about 80° C. The operating pressure of the etherification reaction zones are generally selected to ensure that the feedstreams or charges to the reaction zones and the product streams from the reaction zones remain in the liquid phase during the etherification reaction. Typical pressures are in the range of from about 30 psig to about 300 psig, but as earlier noted, it has been determined that if it is feasible to operate the second etherification reaction zone at operating pressures below 20 psig, significant reductions in the energy consumption in operating first separation means can be achieved thus making the novel process described herein much more economical to operate than the prior art processes. However, in most circumstances, the etherification reactions should be conducted in the liquid phase. Generally, the liquid hourly space velocity (LHSV) of feed to the etherification reactors will be in the range of from about 1 hour$^{-1}$ to about 20 hours$^{-1}$; but, preferably, the LHSV can be in the range of from about 2 hours$^{-1}$ to about 10 hours$^{-1}$. Most preferably, the LHSV can be in the range of from 3 hours$^{-1}$ to 5 hours$^{-1}$.

The etherification reaction is that which selectively reacts tertiary olefins with alcohol, which is preferably methanol, to form a tertiary ether compound. The etherification reaction is an equilibrium type reaction that can be represented as follows:

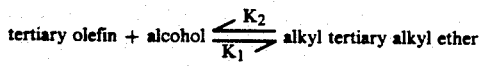

$$\text{tertiary olefin} + \text{alcohol} \underset{K_1}{\overset{K_2}{\rightleftharpoons}} \text{alkyl tertiary alkyl ether}$$

Due to the values and temperature dependencies of the equilibrium constants of the aforementioned reaction, the equilibrium condition which favors the formation of the tertiary ether product is a low reactor temperature condition; but, in any event, because the etherification reaction is an equilibrium type reaction, the percent conversion of the tertiary olefin contained in a reaction zone to an ether product is thermodynamically limited. It has been surprisingly found that it is possible to have a high tertiary olefin conversion etherification process with low energy operating cost by carrying out the etherification process in two reaction stages with the second reaction stage following a separation step, which necessarily follows a first reaction stage, and by utilizing an intermediate stream from the separation step as a feed to the first reaction stage. Accordingly, an intermediate stream from the separation step is passed to the first reactor stage of the etherification process to thereby lower energy consumption by the overall process.

The acid ion exchange catalysts utilized in the etherification reaction zones of the present invention are relatively high molecular weight carbonaceous material containing at least one SO$_3$H functional group. These catalysts are exemplified by the sulfonated coals ("Zeo-Karb H", "Nalcite X" and "Nalcite AX") produced by the treatment of bituminous coals with sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalysts are preferred for use in the present invention. These catalysts include the reaction products of phenolformaldehyde resins with sulfuric acid ("Amberlite IR-1", "Amberlite IR-100" and "Nalcite MX"). Also useful are the sulfonated resinous polymers of coumarone-indene with cyclopentadiene, sulfonated polymers of coumarone-indene with cyclopentadiene, and furfural and sulfonated polymers of cyclopentadiene with furfural. The most preferred cationic exchange resins are strongly acidic exchange resins consisting essentially of sulfonated polystyrene resin. These resins are manufactured and sold commercially under various trade names such as "Dowex 50", "Nalcite HCR" and "Amberlyst 15". As commercially obtained, they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalysts for the etherification.

Now referring to FIG. 1, there is provided a schematic representation of etherification process system 10 having a first reaction section 12 and a second reaction section 14.

An alcohol feedstream, which preferably contains methanol, is charged to etherification process system 10 via conduit 18. A hydrocarbon feedstream, containing the reactive isoolefins of either isobutylene or isoamylene, or both, and a nonreactive diluent, is charged via conduit 20 to etherification process system 10. The two streams passing through conduits 18 and 20 are mixed together prior to passing by way of conduit 22 to first etherification reactor vessel 24, which defines a first etherification reaction zone wherein is contained an acidic ion exchange resin catalyst as described herein. The first etherification reaction zone is operated under suitable etherification reaction conditions so as to react at least a portion of the tertiary olefins with the alcohols contained in the feedstream to first etherification reactor vessel 24 to produce a first etherification reactor effluent.

To control the reaction temperature within the first etherification reaction zone, an optional portion of the first etherification reactor effluent can be recycled via conduits 27 and 22 as a feed to first reactor vessel 24. The remaining portion of the first etherification reactor effluent passes via conduit 26 to first separation means 28 for separating its feeds into a first bottoms stream, comprising the ether product produced from the reactions that take place in first etherification reactor vessel 24; a first overhead stream, comprising unreacted alcohols, unreacted tertiary olefins and at least a substantial amount of the compounds contained in the incoming hydrocarbon feedstream that are nonreactive under the etherification reaction conditions at which first etherification reactor vessel 24 operates; and an intermediate or sidedraw stream, comprising unreacted tertiary olefins. First separation means 28 is any equipment or process which can suitably separate ether compounds from a stream comprising primary alcohols and hydrocarbon compounds, but it is preferred for first separation means 28 to be a typical conventional distillation column that defines a separation zone and which can comprise a rectifying zone and a stripping zone. In the novel process described herein, first separation means 28, or in the preferred case, first distillation column or first fractionator 28, will separate the first etherification reactor effluent into a first overhead stream containing primary alcohols and hydrocarbons that passes as a vapor overhead stream via conduit 30 through overhead condenser 32, which is interposed in conduit 30, and to overhead accumulator 34; a bottoms stream containing a first ether product that is conveyed from fractionator 28 via conduit 36; and a sidedraw stream containing tertiary olefins that is recycled by way of conduit 38 to the feedstream to first etherification reactor vessel 24.

Second etherification reactor vessel 40 defines a second etherification reaction zone wherein is contained an acidic ion exchange resin catalyst identical to the type utilized in the first etherification reaction zone. The overhead condenser 32 defines a heat transfer zone utilized for removing heat energy from the overhead stream leaving first separation means 28 to provide a condensate which passes to overhead accumulator 34. Overhead accumulator 34 defines a phase separation zone and phase separation means for separating vapor and liquid. The vapor phase passes from overhead accumulator 34 via conduit 42 for further processing downstream. At least a portion of the condensed overhead stream passes to second etherification reactor vessel 40 by way of conduit 44 and an optional remaining portion of the condensed overhead stream passes to first fractionator 28 as a feed, preferably as a reflux, via conduit 46.

The second etherification reactor effluent stream leaves second etherification reactor vessel 40 via conduit 48. At least a portion of the second etherification reactor effluent stream passes by way of conduit 48 to second separation means 50. Optionally, a remaining portion of the second etherification reactor effluent stream, after at least a portion of the second etherification reactor effluent stream is passed to second separation means 50 is passed by way of conduit 52 to first separation means 28 as a feed and, preferably, as a reflux.

Second separation means 50 can be any suitable means for separating the at least a portion of said second etherification reactor effluent stream into a second bottoms stream, comprising the ether product produced by the reaction of tertiary olefins with primary alcohols in second etherification reactor vessel 40, and a second overhead stream, comprising hydrocarbons, primary alcohols and any by-products produced in the previous two etherification reaction zones. It is preferable, however, for second separation means 50 to be a conventional distillation column or fractionator which defines a separation zone. In the use of the preferred distillation equipment, the bottoms product from second separation means 50 will comprise ether compounds produced in second etherification reactor vessel 40 and passes from second separation means 50 by way of conduit 54. The overhead stream from second separation means 50 will comprise unreacted hydrocarbons, primary alcohols and undesirable reaction by-products that pass by way of conduit 54 to downstream processing.

As an additional embodiment of the inventive process, it has been found that process improvements are obtainable by charging at least a portion of the bottoms product from second separation means 50 to first separation means 28. Thus, a portion of the bottoms product from second separation means 50 can be fed to first separation means 28 via conduit 56 and the remaining portion of the bottoms product from second separation means 50 can pass downstream by way of conduit 58.

The following example is presented in further illustration of the invention.

EXAMPLE I

The following calculated example is to illustrate the benefits achievable from the novel process as illustrated in FIG. 1 when compared with a similar process, but one which does not have the improvements of the inventive process. The comparative process, or base process, is different from the process of this invention in that it does not have a sidedraw recycle stream to the first reactor, and it has a significantly lower second fractionator recycle to the first fractionator than that of the inventive process. Table I shows the feedstream composition to the etherification process, and Table II provides pertinent material and energy balance information for the base and inventive processes. The olefin conversion across the etherification process in all cases is fixed at 90 percent, the liquid hourly space velocity (LHSV) is kept at a constant 2.5 LHSV based on fresh hydrocarbon feed plus methanol.

TABLE 1

| Feed to first reactor of etherification process | | |
|---|---|---|
| | Hydrocarbon Feed (lb mole/hr) | Methanol Feed (lb mole/hr) |
| i-pentane | 33.3 | — |
| 1-pentene | 22.9 | — |
| 2-m-1-butene | 50.0 | — |
| n-pentane | 112.0 | — |
| tr-2-pentene | 195.0 | — |
| cis-2-pentene | 97.5 | — |
| 2-m-2-butene | 262.7 | — |
| cyclopentene | 34.6 | — |
| cyclopentane | 11.2 | — |
| methanol | — | 312.4 |
| TAME | — | — |
| dimethyl ether | — | — |
| H$_2$O | — | 1.7 |
| Total lb mole/hr | 819.3 | 314.1 |

TABLE 2

| Material and energy balances for etherification process for base case and alternative cases | | | | | |
|---|---|---|---|---|---|
| | | Second Stage | Sidedraw Recycle | | |
| Stream Flow (Mols/Hr) | Base Case | Recycle | 300 | 600 | 1000 |
| Total first reactor charge | 3730.0 | 3729.0 | 3862.0 | 3962.0 | 4043.0 |
| Total second reactor charge | 2165.0 | 2210.0 | 1911.0 | 1933.0 | 1819.0 |
| Second fractionator bottoms | 36.0 | 81.0 | 86.0 | 80.0 | 83.0 |
| Recycle to first fractionator | 937.0 | 938.0 | 1229.0 | 15250 | 1922.0 |
| Feed to first fractionator | 569.0 | 614.0 | 620.0 | 613.0 | 615.0 |
| Feed to second fractionator | 2596.0 | 2596.0 | 2429.0 | 2229.0 | 1910.0 |
| Second reactor recycle to first fractionator | 1508.0 | 1508.0 | 1212.0 | 1244.0 | 1131.0 |
| Sidedraw | 0 | 0 | 300.0 | 600.0 | 1000.0 |
| Duties (Btu/Hr) | | | | | |
| First overhead condenser | 25,624,300 | 26,123,300 | 22,620,100 | 22,841,300 | 21,508,100 |
| First reboiler | 22,854,900 | 23,423,600 | 20,044,100 | 19,956,400 | 18,388,200 |
| Second overhead condenser | 14,255,700 | 12,527,000 | 12,821,600 | 12,876,600 | 13,012,400 |
| Second reboiler | 12,342,100 | 10,668,500 | 11,152,600 | 11,172,900 | 11,413,500 |
| Heat3 | (1,048,960) | (904,837) | (698,083) | (755,938) | (643,131) |
| Total Cool Duty (But/Hr) | 40,928,960 | 39,555,137 | 36,139,783 | 36,473,838 | 35,163,631 |

TABLE 2-continued

Material and energy balances for etherification process for base case and alternative cases

| Stream Flow (Mols/Hr) | Base Case | Second Stage Recycle | Sidedraw Recycle | | |
|---|---|---|---|---|---|
| | | | 300 | 600 | 1000 |
| Total Reboil, (Btu, Hr) | 35,197,000 | 34,092,100 | 31,196,700 | 31,129,300 | 29,801,700 |

As can be seen from the data presented in Table 2, an improvement in energy consumption of the etherification process can be achieved by recycling a sidedraw cut from the first fractionator to the first etherification reactor. There is presented three separate cases in which a sidedraw stream is recycled including a sidedraw recycle of 300 moles per hour, 600 moles per hour, and 1000 moles per hour. In each case, the total reboiler duty required to operate the etherification process is significantly decreased over that required to operate the base case process which includes no sidedraw recycle. It should also be noted that the data presented in Table 2 show that an increase in second stage product recycle as a feed to the first fractionator results in a reduction in the overall process energy consumption. Thus, the data demonstrate the unexpected benefits from operating a two reactor stage etherification process having both a sidedraw recycle and a second stage product recycle.

Reasonable variations and modifications are possible within the scope of the foregoing disclosure, drawings and appended claims.

That which is claimed is:

1. A process, comprising the steps of:
   contacting an alcohol and a feedstream comprising tertiary olefins with a first acid catalyst in a first etherification reaction zone so as to form a first reaction mixture comprising ether, tertiary olefins, and alcohol;
   passing said first reaction mixture to separation means for separating said first reaction mixture into a first overhead stream, a first bottoms stream, and an intermediate stream wherein said first overhead stream comprises alcohol, said first bottoms stream comprises ether, and said intermediate stream comprises tertiary olefins;
   contacting said first overhead stream with a second acid catalyst in a second etherification zone so as to form a second reaction mixture comprising ether;
   introducing said intermediate stream into said feedstream; and
   separating said second reaction mixture into a second overhead stream and a second bottoms stream wherein said second overhead stream comprises alcohol and said second bottoms stream comprises ether.

2. A process as recited in claim 1, wherein said alcohol is methanol.

3. A process as recited in claim 1, wherein said tertiary olefins are selected from the group consisting of isobutylene, isoamylene and mixtures thereof.

4. A process as recited in claim 1, wherein said ether is selected from the group consisting of methyl tertiary butyl ether (MTBE), methyl tertiary amyl ether (TAME), and mixtures thereof.

5. A process as recited in claim 1, wherein the molar ratio of said alcohol to said tertiary olefins contacted in said first etherification reaction zone and in said second etherification reaction zone is in the range of from about 0.5:1 to about 4:1.

6. A process as recited in claim 1, wherein the process conditions within said first etherification reaction zone and within said second etherification reaction zone are such that the temperature is in the range of from about 30° C. to about 120° C. and the pressure is in the range of from about 30 psig to about 300 psig.

7. A process as recited in claim 1, wherein the liquid hourly space velocity of the feed to said first etherification reaction zone and to said second etherification reaction zone is in the range of from about 1 hour$^{-1}$ to about 20 hours$^{-1}$.

8. A process as recited in claim 1, further comprising the step of:
   passing said second bottoms stream to said separation means.

9. A process as recited in claim 8, further comprising the step of:
   passing a portion of said second reaction mixture to said separation means.

* * * * *